United States Patent
Rogozinski

[11] Patent Number: 6,159,213
[45] Date of Patent: Dec. 12, 2000

[54] CERVICAL PLATE

[76] Inventor: Chaim Rogozinski, 3223 Front Rd., Jacksonville, Fla. 32217

[21] Appl. No.: 09/165,421

[22] Filed: Oct. 2, 1998

[51] Int. Cl.[7] .................................................. A61B 17/56
[52] U.S. Cl. .............................. 606/70; 606/61; 606/69; 606/71
[58] Field of Search ................... 606/69, 70, 71, 606/61; 623/17

[56] References Cited

U.S. PATENT DOCUMENTS

| | | | |
|---|---|---|---|
| 1,025,008 | 4/1912 | Miner | 606/71 |
| 5,108,395 | 4/1992 | Laurain | 606/61 |
| 5,344,421 | 9/1994 | Crook | 606/61 |
| 5,681,311 | 10/1997 | Foley et al. | 606/61 |
| 5,728,127 | 3/1998 | Asher et al. | 606/61 |

Primary Examiner—Michael Buiz
Assistant Examiner—Julian W. Woo
Attorney, Agent, or Firm—Edward S. Irons

[57] ABSTRACT

A cervical plate for use alone or in combination with a cervical link system is described. The cervical plate may be generally quadrangular with a bone screw aperture at each corner area. An oval or elongated bone screw aperture is positioned in the central area of the cervical plate to accommodate intercalation of a bone screw and consequent vertical positioning of the plate. The plate may be secured to at least one link of a cervical link system or used to facilitate revision surgery.

7 Claims, 3 Drawing Sheets

CERVICAL PLATE

RELATED APPLICATIONS

This application is related to pending U.S. applications Ser. No. 08/898,862 filed Jul. 23, 1997 and Ser. No. 08/962,838 filed Nov. 3, 1997. The specification of each of these two United States applications is incorporated herein by reference.

FIELD OF THE INVENTION

This invention relates to a cervical plate useful in association with cervical link systems as described, for example, in U.S. Pat. No. 5,716,357. More particularly, the invention relates to a cervical plate which may be connected to at least one link component of a cervical link system.

BACKGROUND OF THE INVENTION

Known cervical link systems include a plurality of links secured in chain-like fashion by bone screws to adjacent vertebrae. As shown by FIGS. 1A and 1B of U.S. Pat. No. 5,716,357, the links may be flat plates having bone screw apertures at opposite ends. For treatment of lordosis, or hyphosis, or for other reasons, the links may be contoured as shown by FIGS. 8A and 8B of U.S. Pat. No. 5,716,357.

Chain-like constructs of links to be secured by the FIG. 2 bone bolts and associated washers and lock nuts to adjacent vertebrae are shown by FIGS. 4 and 5 of U.S. Pat. No. 5,716,357. Cross-tie mechanisms in the form of one or more links to provide quadrilateral stabilization of adjacent chain-like constructs are shown by FIGS. 4 and 6 of U.S. Pat. No. 5,716,357.

A need exists for a cervical plate useful alone or for connection to a cervical link system as a cross-tie or during revision type surgery.

SUMMARY OF THE INVENTION

The invention is a cervical plate useful per se or as connected to at least one link of a cervical link system. The cervical plate may be included as an initial component of a link system implant. It may be connected to a previously implanted link during revision surgery. Cross-tie connection of the plate to chains of links secured to adjacent vertebrae provides a quadrilateral construct that stabilizes the chains torsionally and in the frontal plane.

Embodiments of the invention may use the bone bolts and lock nuts described in U.S. Pat. No. 5,716,357. The cervical plate may be precontoured for treatment of spinal conditions such as hyphosis and lordosis, or for other reasons. It may span a plurality of vertebrae, for example, three vertebrae, and so facilitate maintenance of a bone graft in position for fusion between two vertebrae.

DETAILED DESCRIPTION OF THE INVENTION

One specific embodiment of the invention is described by reference to the Figures.

Figure 1:
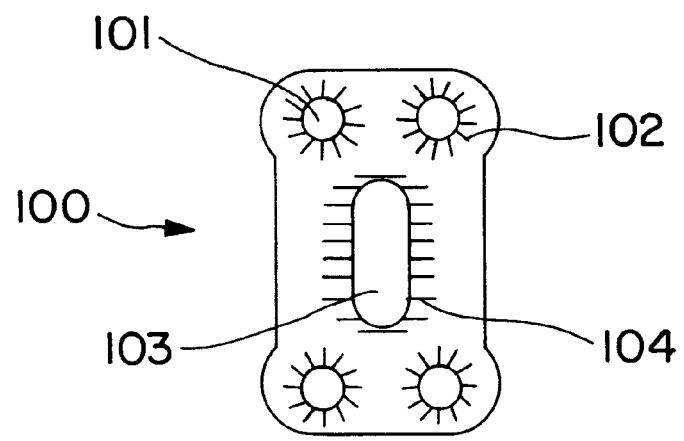
FIG. 1 is a top view of a cervical plate.
Figure 5:
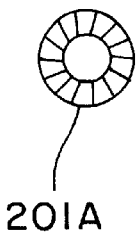
FIGS. 5 and 5A indicate transverse and radial serrations on end caps and lock nuts for use in cervical plate constructs.
Figure 7:
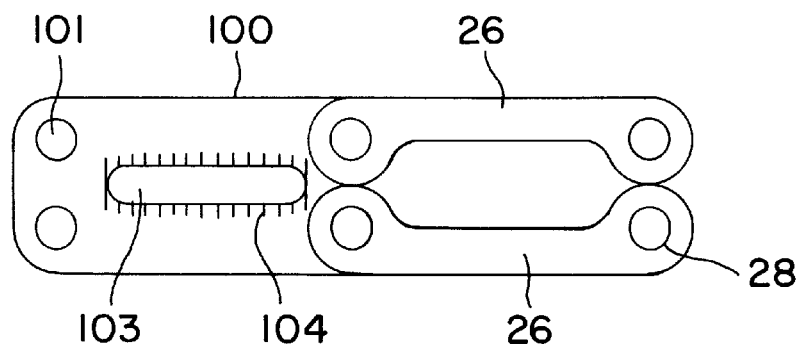
FIG. 7 depicts a cervical plate connected to two links of the cross-link system as shown by FIG. 1B of U.S. Pat. No. 5,716,357.

FIG. 1 illustrates a cervical plate 100 having an aperture 101 at each corner to accommodate a bone screw (not shown). The periphery of the bone screw apertures 101 have optional radial serrations 102 for cooperation with optional bone screws and cap radial serrations 201A as shown by FIG. 5. A central oval slot 103 to accommodate bone screw intercalation has optional lateral serrations 104 for cooperation with optional end lateral cap serrations as shown FIG. 5. The cervical plate may be viewed as a unit structure of two prior art links as shown by FIG. 7.

Figure 2:
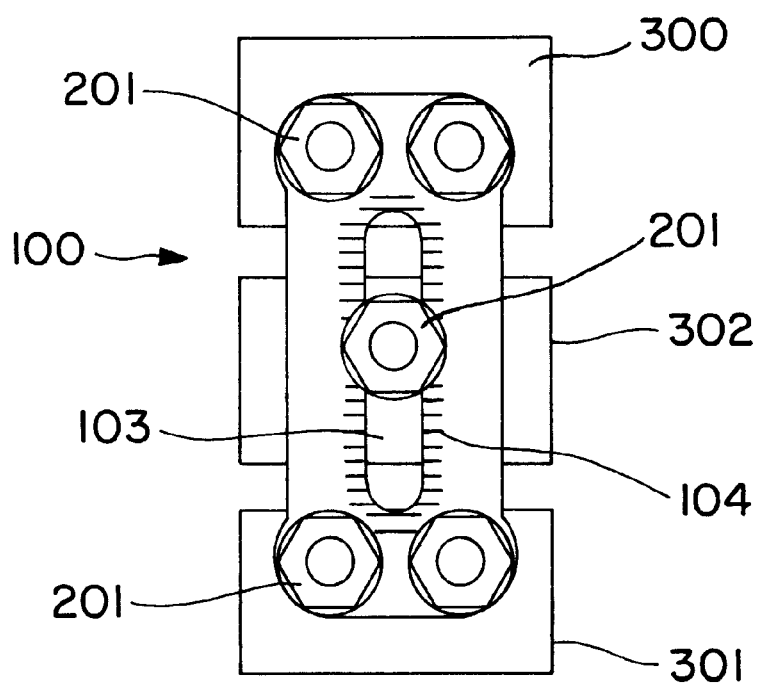
FIG. 2 is a frontal projection showing a contoured cervical plate attached by bone screws to three vertebrae.
Figure 5A:

FIG. 2 illustrates a cervical plate 100 secured to proximal and distal vertebrae 300, 301 and an intermediate vertebra 302. The plate 100 is shown secured to proximal and distal vertebrae 300, 301 and to the intermediate vertebra 302 by bone screws (not shown) having end caps 201. The end cap 201 for the bone screw (not shown) intercalated in slot 103 and secured to the intermediate vertebra 302 may have lateral serrations 201A (see FIG. 5A) to cooperate with the lateral serrations 104 adjacent the central oval slot 103.

Figure 3:
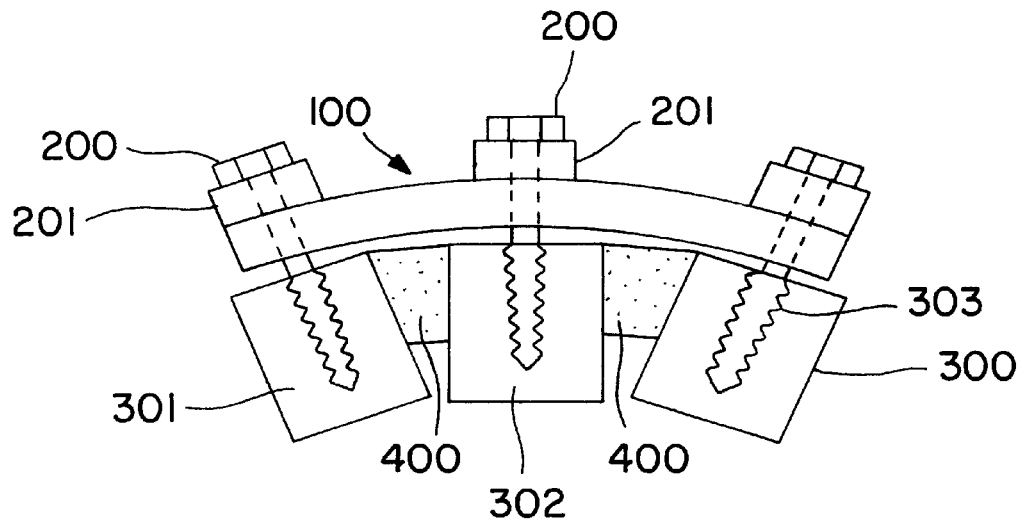
FIG. 3 is a lateral projection of the FIG. 2 construct. Bone grafts in position for fusion are shown between the vertebrae.

The FIG. 3 lateral proportion of the FIG. 2 construct in which the cervical plate 100 is contoured. Conventional procedures for disc surgery include partial or total excision of the injured disc portion (discectomy) and replacement of the excised disc with biologically acceptable plugs or bone graft wedges. The grafts are driven between adjacent vertebrae to maintain normal intervertebral spacing and to achieve, over a period of time, bony fusion with the plug and opposed vertebrae. Consistent with such procedures, FIG. 3 depicts bone grafts 400 in position for fusion between vertebrae 300, 302 and 302, 301.

Figure 4:
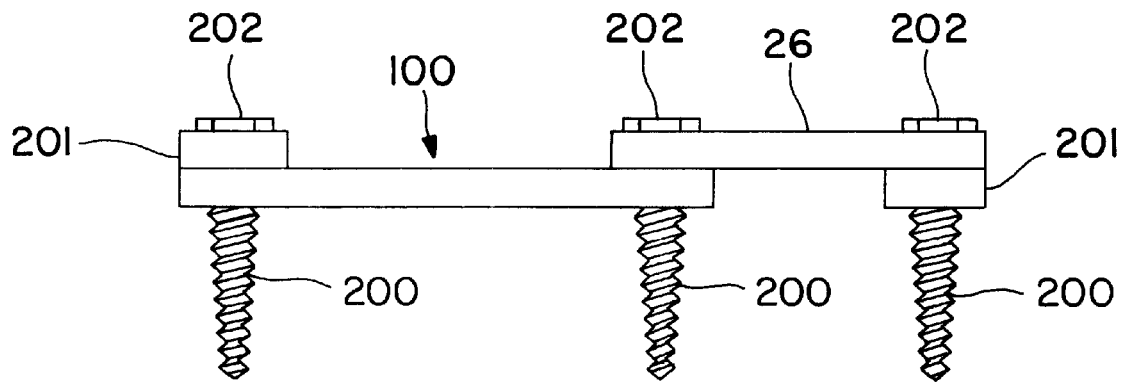
FIG. 4 is a lateral view of a cervical plate and link construct including bone screws.
Figure 6:
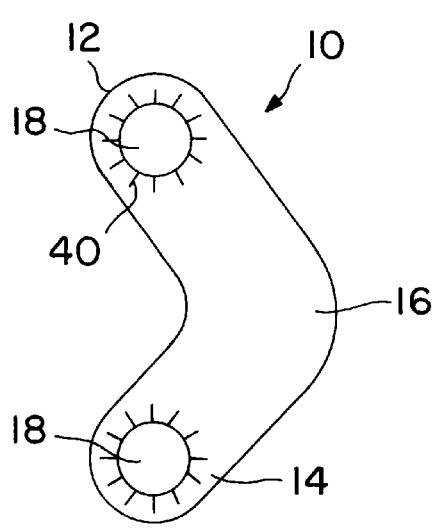
FIGS. 6 and 6A (prior art) illustrate links as shown by FIGS. 1A and 1B of U.S. Pat. No. 5,716,357.
Figure 6A:
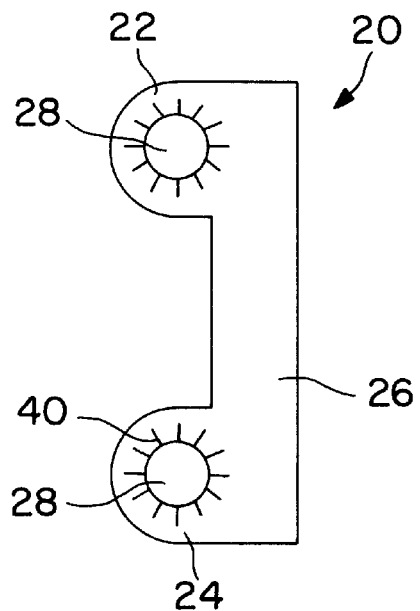

FIG. 4 illustrates a plate and link construct. The construct includes a plate 100, a prior art cervical link 26 (see FIG. 6A), bone screws 200, bone screw end cap 201, and bone screw lock nuts 202.

Bone screws and lock nuts useful in this invention are illustrated by FIG. 2 and described in the specification of U.S. Pat. No. 5,716,357. End caps may occupy otherwise exposed threaded portions of bone screws. The end caps provide appropriate spacing between the components of a cervical link construct. Cervical plates are metal, preferably titanium, and may be of any appropriate size. Preferred plates are about 4 to 20 mm wide and from 12 to 140 mm in length. The invention may include a kit containing a plurality of plates which increase in two millimeter increments in length from 12 to 140 mm bone screws, lock nuts and end caps.

I claim:

1. A kit comprising:

(i) a plate; said plate comprising:
   four spaced apart bone screw apertures in said plate; radial serrations adjacent at least one of said bone screw apertures; an oval slot disposed within the space defined by said spaced apart bone screw apertures; and transverse serrations adjacent said oval slot, and (ii) links each having a central portion and apertured end portions, wherein at least one of said apertured end portions of said link is adapted to be connected by a bone screw to at least one of said bone screw apertures of said plate.

2. A kit according to claim 1 further comprising:

(i) bone screws, one for each of said four apertures in said plate;

(ii) a bone screw for intercalation in said oval slot in said plate;

(iii) lock nuts for each of said bone screws; and (iv) optional end caps for at least one of said bone screws.

3. A construct comprising:

(i) a generally rectangular cervical plate
   wherein said cervical plate comprises:
   (a) bone screw apertures adjacent corners of said plate and radial serrations adjacent at least one of said bone screw apertures;
   (b) an oval slot disposed centrally therein;
   (c) transverse serrations around the periphery of said slot; and (ii) a link,
   wherein said link comprises a central portion connecting apertured end portions and
   wherein at least one of said apertured end portions of said link is connected by a bone screw to at least one of said bone screw apertures of said cervical plate.

4. The claim 3 construct, wherein said cervical plate is precontoured.

5. The claim 4 construct, wherein said cervical plate is precontoured for the treatment of a spinal condition comprising hyphosis or lordosis.

6. The claim 4 construct, wherein said plate is dimensioned to span a plurality of vertebrae for maintenance of a bone graft in position for fusion between two vertebrae.

7. A construct comprising:

(i) a cervical plate according to claim 1, (ii) bone screws positioned within the said four bone screw apertures in said plate, and (iii) a bone screw intercalated within said oval slot in said plate.

* * * * *